United States Patent [19]
Nordhauser et al.

[11] Patent Number: 5,849,333
[45] Date of Patent: Dec. 15, 1998

[54] DELAMINATED TRANSPARENT TALC

[75] Inventors: Mary Ann Nordhauser, Brighton, Mich.; James Robert Anderson, Anniston, Ala.

[73] Assignee: American Westmin, Inc., Oxford, Ala.

[21] Appl. No.: 416,078

[22] Filed: Apr. 4, 1995

[51] Int. Cl.$^6$ .............. A61K 9/14; A61K 7/02; A61K 33/00; C04B 14/30

[52] U.S. Cl. .............. 424/489; 424/69; 428/402; 514/770; 514/844; 514/951; 106/626

[58] Field of Search .............. 424/400, 489, 424/692, 69; 428/402; 514/951, 844, 770; 106/626

[56] References Cited

U.S. PATENT DOCUMENTS

| | | | |
|---|---|---|---|
| 3,102,855 | 9/1963 | Brown et al. | 209/164 |
| 3,414,201 | 12/1968 | Bixby | 241/4 |
| 3,806,043 | 4/1974 | Roe | 241/4 |
| 3,965,241 | 6/1976 | Baak et al. | 423/155 |
| 4,562,215 | 12/1985 | Carter et al. | 523/220 |
| 4,618,528 | 10/1986 | Sacks et al. | 428/216 |
| 4,956,019 | 9/1990 | Noguchi et al. | 106/415 |
| 5,019,446 | 5/1991 | Bunnell | 428/324 |
| 5,037,034 | 8/1991 | Duncan | 241/247 |
| 5,137,217 | 8/1992 | Duncan | 241/4 |
| 5,308,516 | 5/1994 | Chiddick | 250/30 |
| 5,326,806 | 7/1994 | Yokoshima et al. | 524/411 |
| 5,340,582 | 8/1994 | Sugasawa et al. | 424/401 |
| 5,352,441 | 10/1994 | Mausner | 514/772.5 |
| 5,356,617 | 10/1994 | Schlossman | 424/401 |

FOREIGN PATENT DOCUMENTS 3728404  9/1989  Germany .

OTHER PUBLICATIONS

"Cosmetic Talc" by Ronald W. Greya, et al. reprinted from Drug & Cosmetics Industry, May, 1987.

Primary Examiner—Edward J. Webman
Attorney, Agent, or Firm—Selitto & Associates

[57] ABSTRACT

A delaminated talc has a plurality of high aspect ratio, smooth surface particles. The aspect ratio of the particles is determined by dividing their extent along an upper surface thereof by their thickness. The upper surface is substantially parallel to the lamellar interface direction and the thickness is measured perpendicularly to the interface direction. The upper, lower and side surfaces of the particles are smooth, lacking acute angularity and staircase effect which give rise to increased coefficient of friction and light scattering. The talc is especially suitable in cosmetic and pharmacologic preparations due to its high degree of transparency, skin adhesiveness, lubricity and spreadability.

10 Claims, 7 Drawing Sheets

DELAMINATED TRANSPARENT TALC

FIELD OF THE INVENTION

The present invention relates to talc, products including talc, and, more specifically, to a new and improved talc exhibiting high transparency, skin adhesiveness, lubricity and spreadability, which is particularly suitable for use in cosmetic and pharmaceutical preparations.

BACKGROUND OF THE INVENTION

Talcs have a wide range of industrial, medical, pharmaceutical and cosmetic applications including use as a component in flame retardants, sealing compounds, magnetic tapes, plastic modifiers, dental implants, chewing gum, ceramic products, pharmaceuticals, nail enamel, soap, detergents, hair products, antiperspirants, sunscreens, acne remedies and antimicrobials.

Talcs have been found in various parts of the world including the United States, Canada, the People's Republic of China, Finland, Russia, France, Australia, India, Austria, Italy, Egypt, Republic of Korea and Norway. In the United States, talc deposits have been mined in Texas, Vermont, New York, Montana and California.

While a variety of natural minerals are usually present in naturally occurring deposits, talc is generally regarded as being composed of hydrous magnesium silicates (i.e., $Mg_3SiO_{10}(OH)_2$), with theoretically 31.7% MgO, 63% $SiO_2$ and 4.8% $H_2O$ by weight. Pure talcs, whose crystal structure can be foliated, lamellar or massive, generally exhibit softness, hydrophobicity and slipperiness. Depending on the amount of impurities and minerals present in talcs, commercially available talcs may be harder than pure talcs. Naturally occurring talcs range in color from white to green and brown, with pure talcs in a powder form generally exhibiting varying degrees of whiteness. High quality talcs typically are rated at 90–95% on the General Electric brightness scale. The refractive index of talc ranges from about 1.54 to 1.59 with the specific gravity of talcs ranging from 2.7 to 2.8.

Figure 1:
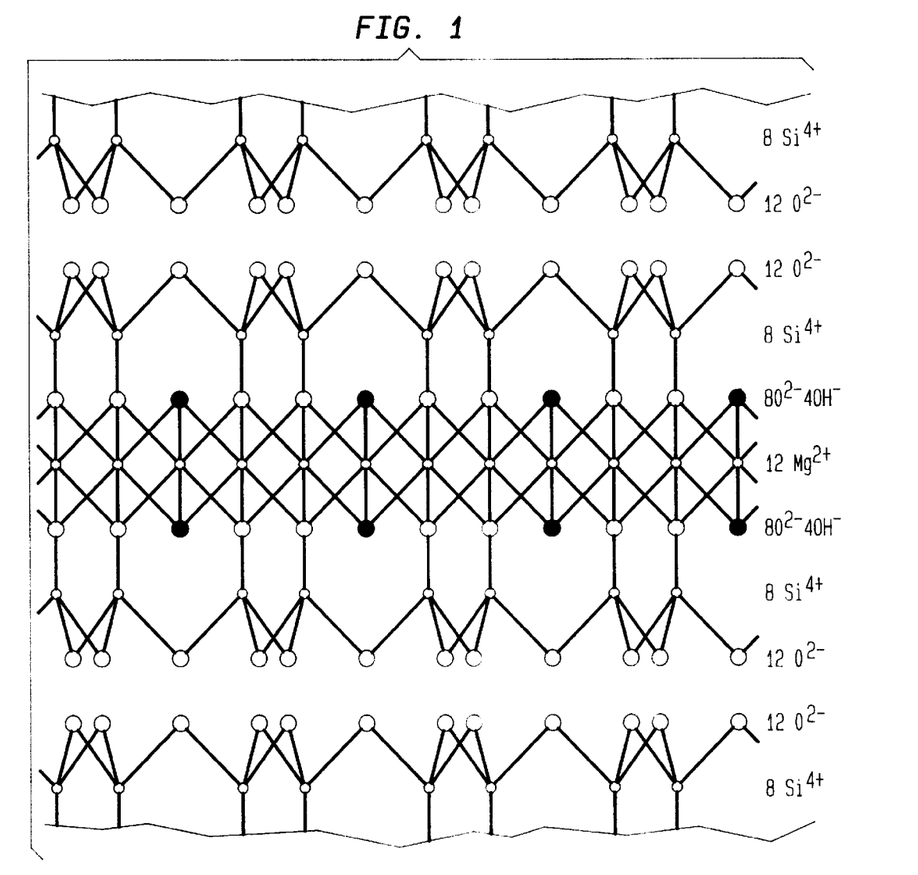
FIG. 1 is a simplified structural formula representing the crystalline structure of talc.

With reference to FIG. 1, pure talcs are made up of a plurality of crystal layers or laminae, each of which includes a brucite sheet positioned between a pair of silica sheets. The laminae are discrete and electrically neutral, being held in relative superimposition by weak van der Waals forces. As a result, the crystal layers "slide" over one another readily if subjected to shearing force. Due to the relative sliding of crystal layers, talc is known to have a slippery or "greasy" characteristic that has resulted in its use as a lubricant and friction reducer. The degree of slipperiness is highly variable from one talc to another and manufacturing processes can either accentuate or destroy the sliding effect of the crystal layers. Moreover, since the lamellar layers are exquisitely fragile, the ability to maintain lamellar integrity during processing without disrupting the integrity of the surface is extremely difficult. Lamellar talcs also exhibit hydrophobic-organophilic attributes which theoretically translate to skin adhesiveness and spreadability which, together with softness to the touch and lubricity, has led to extensive use in cosmetology and pharmacology.

Because raw talcs typically contain impurities and are not of suitable particle size, they generally need to be comminuted and refined prior to use in industrial, medical, pharmaceutical and cosmetic applications. Raw talcs may be crushed with a jaw or roller crusher and then undergo rotary or flash drying. Talcs may also be ground with roller-type, pendular or ball/pebble mills to form a talc powder having a particle size of from 99 to 99.8% passage through a USBS sieve of 200 mesh with openings of about 74 microns. Historically and for many years, the particle size of about 44 microns has generally been considered to be the optimal fineness for the cosmetic industry. This translates to a about 99% passage rate through a USBS sieve of 325 mesh with openings of about 44 microns.

However, more recently, processes for reducing talcs to subsieve particle sizes (i.e., less than or equal to 30 microns) have been developed. For instance, fluid energy micronizers utilizing super-heated steam may produce talcs having a maximum particle size of as small as 6 microns. Ultrahigh-speed vertical hammer mills can also be used for this purpose if a classification step is included.

Varying efforts have been expended in the talc industry to process raw talcs into smaller and smaller particles. In this respect, its platy or lamellar characteristics present both a benefit and an obstacle in that, while talc particles are easier to fracture along the lamellar interface, inter-plate slip also allows raw talc chunks to escape being drawn between the impinging edges, teeth, grinding surfaces, etc., of the milling apparatus. It has been recognized that a method for achieving more structurally suitable talc particles is to delaminate the raw talcs. While progressively finer comminution has associated benefits, comminution methods which are oblivious to particle shape can also result in detrimental effects, such as, a loss of lubricity and softness to the touch and an increase in opacity.

Whereas the focus of the prior art has primarily been on particle size, there has been a lack of appreciation for the implications of talc particle shape relative to the lamellar interface. The present invention recognizes the effect of talc particle shape and dimensionality relative to the lamina surface and interface upon the observable properties of the resultant talc both alone and in cosmetic preparations.

SUMMARY OF THE INVENTION

The problems and disadvantages associated with conventional talcs are overcome by the present invention which includes a delaminated talc having a plurality of high aspect ratio, smooth surface particles. The aspect ratio of the particles is determined by dividing their extent along an upper surface thereof by their thickness. The upper surface is substantially parallel to the lamellar interface direction and the thickness is measured perpendicularly to the interface direction. The talc is especially suitable in cosmetic and pharmacologic preparations due to its high degree of transparency, skin adhesiveness, lubricity and spreadability.

BRIEF DESCRIPTION OF THE DRAWINGS

For a better understanding of the present invention, reference is made to the following detailed description of exemplary embodiments considered in conjunction with the accompanying drawings, in which.

DETAILED DESCRIPTION OF THE EXEMPLARY EMBODIMENTS

Figure 8:
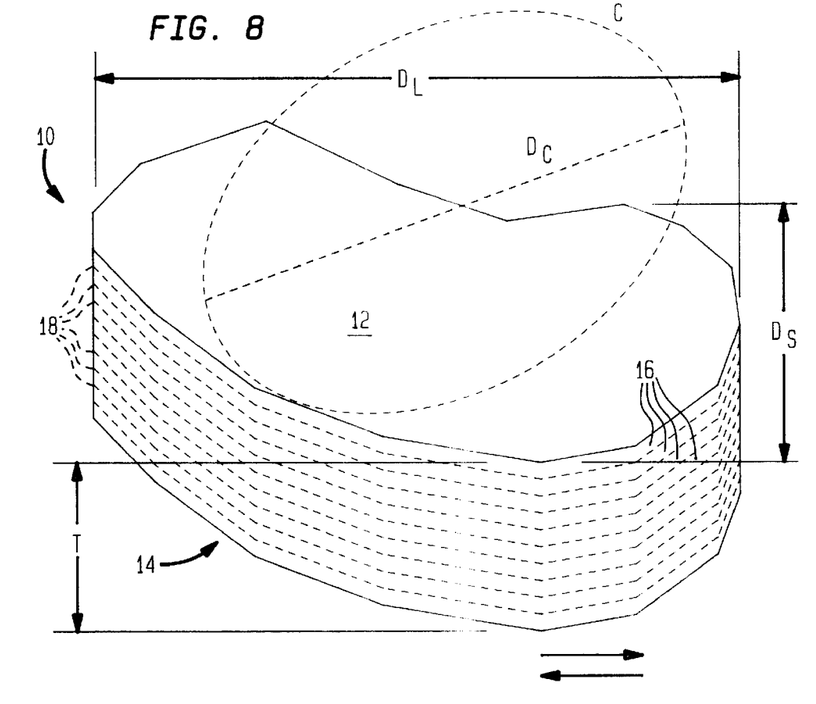
FIG. 8 is an enlarged schematic illustration of one of the particles in accordance with the present invention shown in FIG. 2, showing a lamina and surface structure of same.

Referring to FIGS. 2, 5, 6 and 8, a talc particle 10 in accordance with the present invention has a pair of substantially flat opposing surfaces 12, 14, each generated from a lamellar interface (see FIG. 8). With specific reference to FIG. 8, the particle 10 has a thickness T which is relatively small compared to the large and small dimensions $D_L$, $D_S$ of the surfaces 12, 14, the thickness T ranging from 0.01 to 100 microns, preferably from 0.1 to 75 microns, more preferably from 0.1 to 30 microns. As used herein, "thickness, T" shall be defined as the distance between flat surfaces 12, 14 measured substantially perpendicularly to the laminae 16 and lamellar interfaces 18 (indicated by broken lines). The relationship of the thickness "T" to the surface dimensions $D_L$, $D_S$ may be expressed in terms of the aspect ratio of the particle 10. Which, in the case of talc particles in accordance with the present invention, is 5 or greater. The traditional definition of aspect ratio, which has historically been used to demonstrate particle shape does not completely define the character of the talc particle of the present invention because the dimensions of the talc particle relative to the lamellar interface direction and the smoothness and overall particle size are not considered. We find that aside from particle size, the smoothness of the lamellar surface of platy delaminated talc particles is of critical importance and the photographs of the above described figures exhibit the truly smooth surfaces and more rounded and less bluntly shaped particle of the invention.

In FIG. 8, it is shown that the laminae 16 are of uniform thickness and the lamellar interfaces 18 therefore are substantially parallel to each other and to the flat surfaces 12, 14. The flatness and relative parallelism of the flat surfaces 12, 14 is due to their origin as lamellar interfaces, i.e., the upper and lower layers respectively of silica in the terminal crystal tri-layers of the particle.

Talc particles in accordance with the present invention are characterized as having an extremely uniform surface, substantially free of defects such as "staircase" effect to be discussed hereinafter and rough edges. The talc particles are produced from platy talc having a high degree of delamination, and the particles exhibit smooth surfaces (see FIGS. 2, 5 and 6), high transparency (see FIG. 2), lubricity and skin adhesiveness. A talc produced having visually observable structural smoothness can be demonstrated via SEM, TEM, or optical microscope, etc. Further, the peripheral edges of the particles perpendicular to the surfaces 12, 14 in accordance with the present invention, which classically exhibit rough, debrided sides, will be shown to be smoother and more uniform. Further, it is these features that magnify the degree of lubricity, transparency and adhesion.

The above-described characteristics of the talc in accordance with the present invention are achieved by gentle delamination techniques. More particularly, a mass of raw talc is subjected to compressive forces (i.e. forces perpendicular to lamellar interfaces of the talc) in conjunction with lateral forces (i.e. forces parallel to the lamellar interfaces of the talc). The compressive forces assist in overcoming the van der Waals forces holding the layers of the talc together and thereby allowing the lateral forces to slice the layers apart easily, producing talc particles in conformity with the present invention to a large degree. The thin talc particles are separated from the thick talc particles through a hydraulic classification. This separation step can include conventional apparatus, such as, thickeners, lamella thickeners, hydrosizers, centrifuges, settling tanks and hydraulic classifiers. Two particles of different thicknesses having the same surface profile settle at different rates in a hydraulic medium. The talc particles which have greater thickness and therefore have greater weight settle more quickly than the thin, delaminated talc particles and can thereby be separated from the thin talc particles.

Due to the simultaneous application of compressive forces and lateral forces, the resulting talc particles have extremely smooth surfaces and a high aspect ratio. While talc particles having a high aspect ratio can be selectively produced, talc particles processed via conventional methods, such as a roller/rod mill, which utilizes only simple compressive forces, a jet or fluid energy mill, which utilizes only simple shearing forces and a ball or vertical hammer mill, which utilizes non-delaminating forces, exhibit rough (i.e., non-smooth) surfaces.

Figure 9:
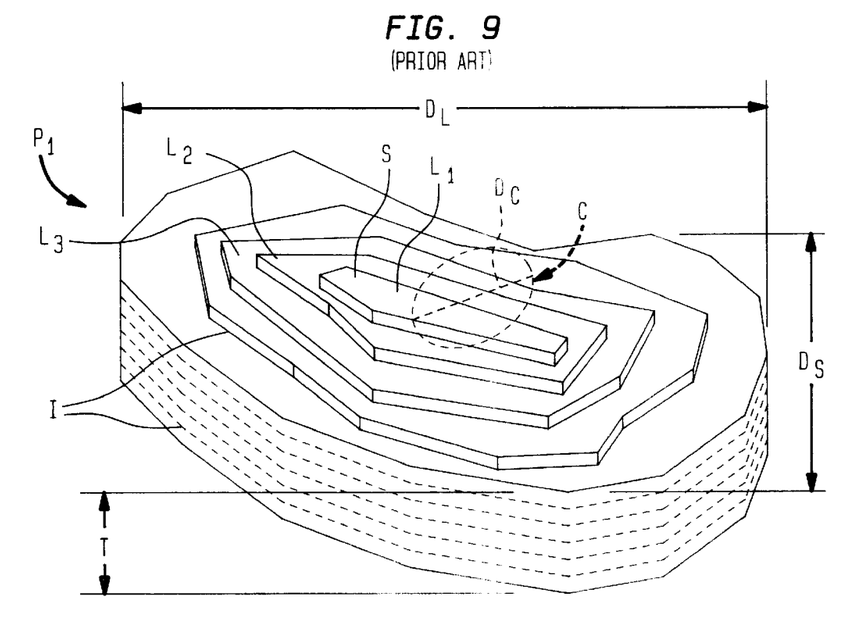
FIG. 9 is an enlarged schematic illustration of a particle of a conventional talc, showing a lamina and surface structure of same.
Figure 10:
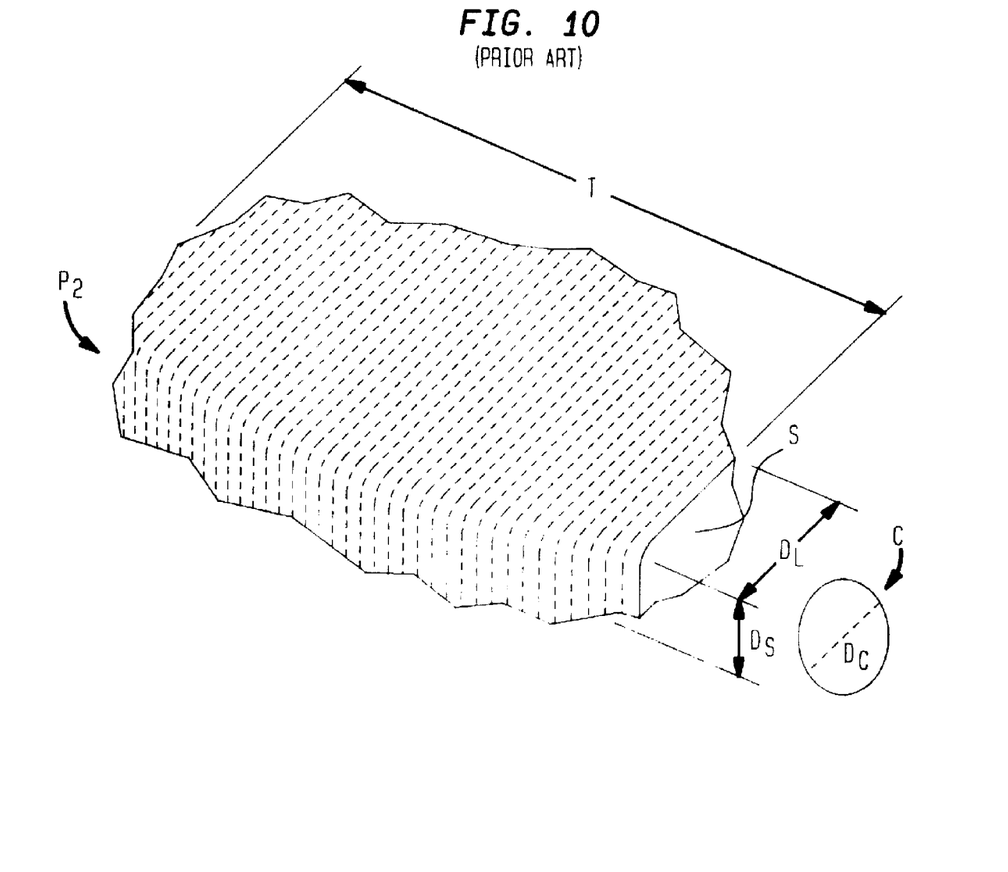
FIG. 10 is a second enlarged schematic illustration of a particle of conventional talc, showing a lamina and surface texture of same.

For the purposes of comparing the talc in accordance with the present invention to conventional talcs, FIGS. 9 and 10 schematically illustrate particles $P_1$ and $P_2$, respectively, of conventional talcs. Referring to FIG. 9, while conventional talc particle $P_1$ has its lamellar interfaces I substantially parallel to a top surface S and a bottom surface (which cannot be seen in FIG. 9) thereof and a thickness T, as defined herein, relatively small compared to the large and small dimensions $D_L$, $D_S$, conventional talc particle $P_1$ does not have smooth and flat top and bottom surfaces which are relatively large compared to the thickness T because of its "staircase" structure. More particularly, each succeeding tri-layer (i.e., crystal layer) of conventional particle $P_1$ moving toward the center and away from the top surface S has a larger area than the proceeding tri-layer, thereby forming the staircase structure. For instance, the top tri-layer $L_1$, which forms the top surface S, is smaller in area than the second tri-layer $L_2$, while the second tri-layer $L_2$ is smaller in area than the third tri-layer $L_3$. As a result of this staircase structure, conventional talc particle $P_1$ has a much smaller effective surface aspect ratio than that of the particle 10 shown in FIG. 8, due to the fact that the thickness of the particle $P_1$ more closely approximates the large and small dimensions $D_L$, $D_S$, of the top surface S. In some instances, the top surface S of conventional talc particle $P_1$ can be made up of a plurality of discrete surfaces, each generated from the tri-layer $L_1$. For example, during processing of the talc, the top surface S is divided into a pair of discrete and independent surfaces, which are smaller than the top surface S and which are separated by a space between them. In such instances, conventional talc particle has an even smaller effective surface aspect ratio than that of the particle shown in FIG. 9.

With reference to FIG. 10, conventional talc particle $P_2$ has a much smaller aspect ratio than that of the particle 10 shown in FIG. 8, due to the fact that the thickness of the particle $P_2$ is much greater relative to the large and small dimensions, $D_L$, $D_S$ of the flat surface S generated from a lamellar interface. More specifically, diameter $D_C$ of equivalent area circle C is small compared to thickness T. In addition, conventional talc particle $P_2$ has a staircase structure similar to the staircase structure associated with conventional talc particle $P_1$ of FIG. 9. More particularly, because ,the surface will show a classic staircase effect where the lamellar surface has been irregularly broken, this will result in an increased faceting effect with subsequent layers displaying varying $D_L$, $D_S$.

Figure 11:
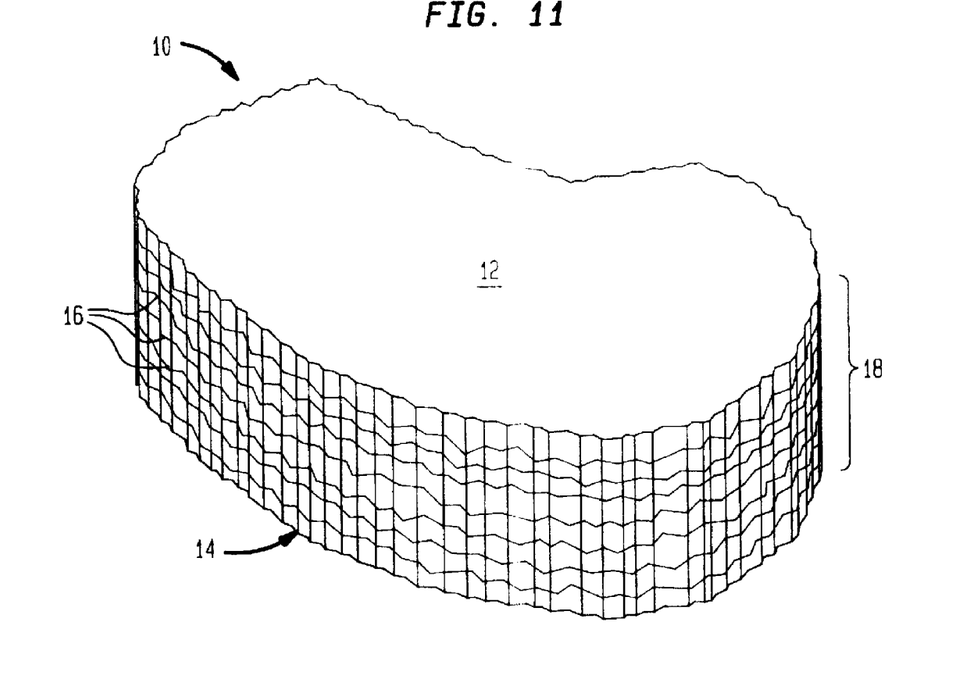
FIG. 11 is a schematic illustration of the particle shown in FIG. 8, showing an outer surface texture of same as effects the directionality of optical transmission.
Figure 12:
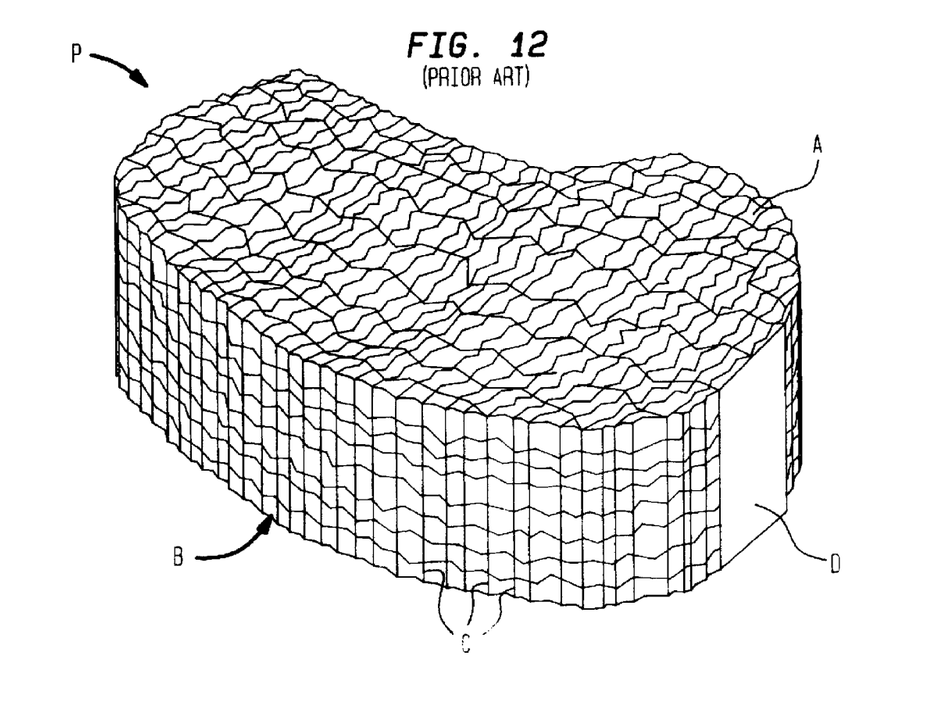
FIG. 12 is a schematic illustration of the particle of FIG. 10 showing outer surface texture as effects light transmission therethrough.

FIGS. 11 and 12 schematically illustrate and compare the surface texture of the particles of talc shown in FIGS. 8 and 10, respectively. It has been observed by the inventors herein that a surface formed by a separation of a pair of adjacent tri-layers of talc is smooth, while a surface formed by a cut across tri-layers of talc is rough. Accordingly, two opposing surfaces 12, 14, which are substantially parallel to the lamellar interfaces 16 and to each other, are smooth and flat, while the peripheral surface 18 of the particle 10, which cuts across the lamellar interfaces, is rough. In FIG. 12, particle P has a major surface A opposing major surface B which is perpendicular to the lamellar interfaces C. The only smooth surface on particle P is D which is generated from a lamellar interface. The particle shown in FIGS. 8 and 11 will exhibit greater transmissivity to light passing though surfaces 12 and 14 because these surfaces are smooth and parallel. The talc in accordance with the present invention can thus be characterized as having a higher transparency which exhibits itself in utilizing 30–40% less pigmentation when formulating pigmented products, as compared to the talc grade represented by FIG. 9. In contrast, the particle shown in FIG. 12 will tend to scatter or diffuse light travelling in a direction through the major surfaces A, B of the particle because these surfaces are rough or irregularly fractured across the lamellar surface.

Figure 5:
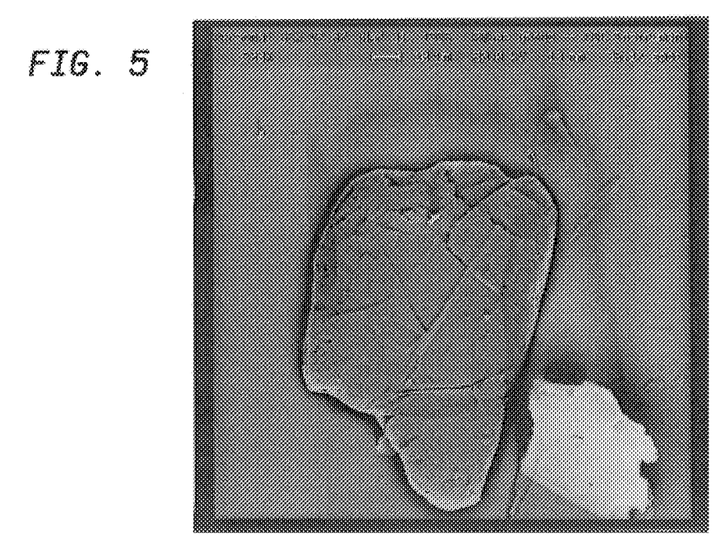
FIG. 5 is a scanning electron micrograph showing a particle of the talc in accordance with the present invention at the magnification of 500x.
Figure 6:
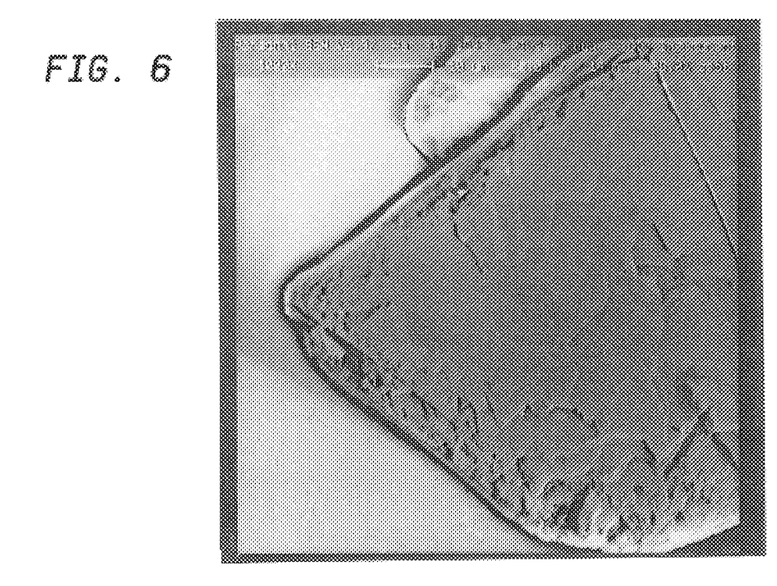
FIG. 6 is a scanning electron micrograph showing another particle of the talc in accordance with the present invention at the magnification of 1000x.
Figure 7:
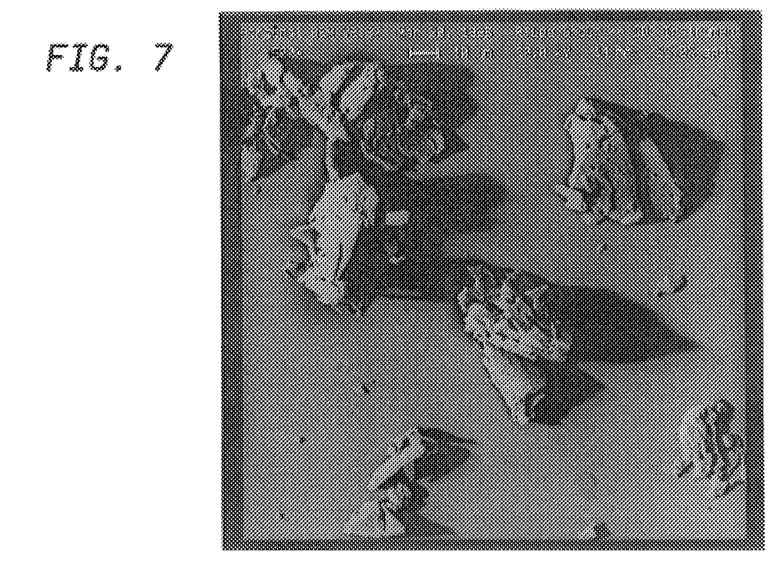
FIG. 7 is a scanning electron micrograph showing particles of a conventional talc (French Talc No. 1) at the magnification of 500x.

With reference to FIGS. 5 and 6, which are scanning electron micrographs of particles of the talc in accordance with the present invention at the magnification of 500×and 1000×, respectively, and to FIG. 7, which is a scanning electron micrograph of particles of a conventional talc at the magnification of 500×, each particle of the talc in accordance with the present invention has an extremely flat smooth upper (and lower) surface and a substantially uniform thickness along its longitudinal axis compared to a particle of the conventional talc which are seen to have rough surfaces and a irregular thickness along its longitudinal axis. Even at a magnification of 1000×, the overall particle surfaces are extremely flat and smooth (see FIG. 6). The smooth surfaces of the particles shown in FIGS. 5 and 6 will allow the passage of light therethrough without substantial diffraction and/or diffusion, making the particles substantially transparent. The rough surfaces of the particles shown in FIG. 7 will scatter and obscure the passage of light therethrough, making the particles substantial opaque or non-transparent.

Figure 2:
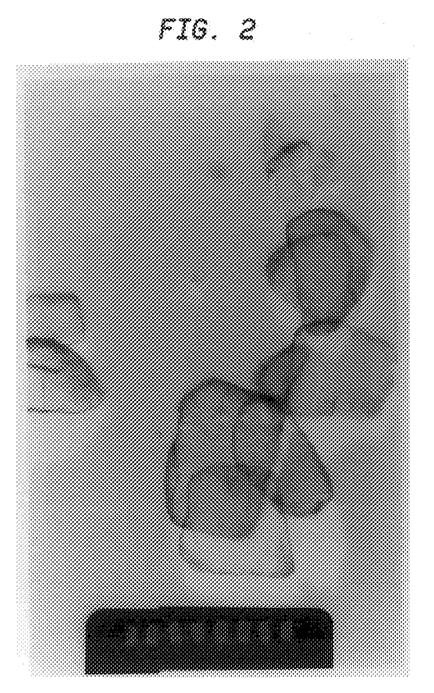
FIG. 2 is an optical micrograph showing particles of a talc in accordance with the present invention at the magnification of 320×.
Figure 3:
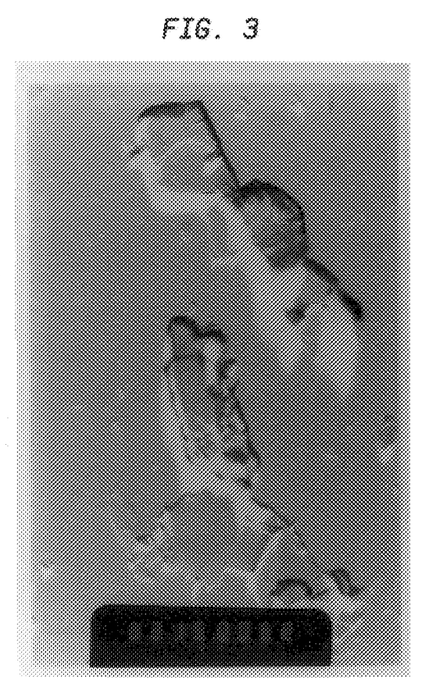
FIG. 3 is an optical micrograph showing particles of a conventional talc (Italian Valchisone) at the magnification of 320×.
Figure 4:
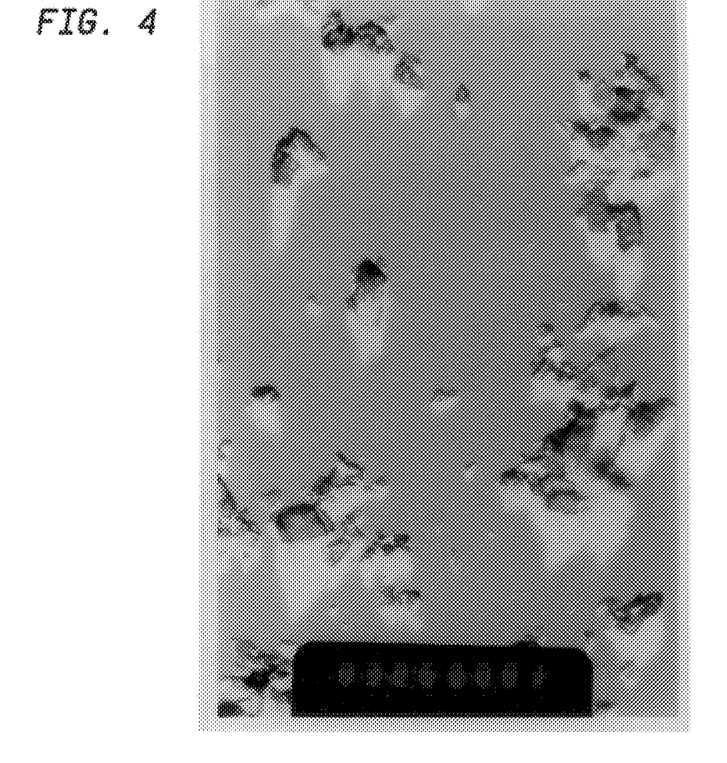
FIG. 4 is an optical micrograph showing particles of another conventional talc (French Talc No. 1) at the magnification of 320×.

With reference to FIGS. 2, 3 and 4, which are optical micrographs of the talc of the present invention and two different types of conventional talc, respectively, the particles shown in FIG. 2 have more uniform surfaces than the particles shown in FIGS. 3 and 4. Further, in examining these talc particles under a light microscope, a light coating of gold was evaporated at a high shadowing angle onto the talc particles, the shadowing angle being chosen such that the shadow area (indicated as bright areas around the portions of the particles in FIGS. 2, 3 and 4) has a length equal to ten times the thickness of the talc particles. The outer edges of the shadow area in FIGS. 2, 3 and 4 therefore reflect the peripheral edges of the particles and the contours of the upper surfaces of the particle proximate the peripheral edges. The outer edges of the shadow of the particles shown in FIG. 2 are softly curved, indicating that the associated peripheral edges of the particles are smooth, while the outer edges of the shadow of the particles shown in FIGS. 3 and 4 are saw-tooth shaped (i.e., have a plurality of sharp edges), indicating that the associated peripheral edges and upper surfaces are rough. Talc particles in accordance with the present invention could be described by noting that the outer peripheral shape of the particle can be approximated by a set of connected curves having radii of curvature greater than $0.125\ D_S$. As a result of the uniform and smooth surfaces, the particles in FIG. 2 are substantially transparent such that the images of underlying particles are clearly transmitted through overlying particles. On the other hand, the particles in FIGS. 3 and 4 are not transparent, and this effect cannot be observed.

Figure 13:
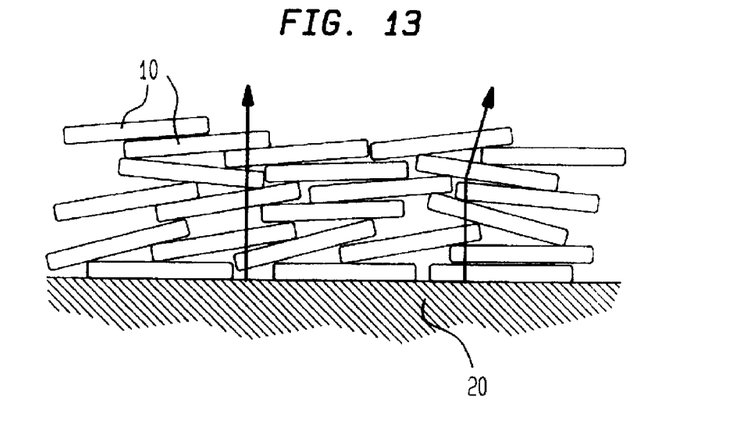
FIG. 13 is a schematic illustration of the particles of the talc in accordance with the present invention deposited on a surface.

The directionality of transmission of light, mentioned above, becomes even more significant to the overall transparency or transmission of a talc film deposited upon a surface, given the effect of the self-orientating characteristic of particles. FIG. 13 illustrates a plurality of particles 10 deposited upon a surface 20, such as a person's skin. While there are a variety of ways to promote talc particles of the present invention to self orient, their interaction with the skin is particularly pertinent herein. Because talc is organophilic, a particle of talc deposited upon skin will seek to orient itself to maximize surface contact. With the high degree of uniformity of the talc particle surface of the present invention, the large flat surfaces of the particles will therefore be attracted to the surface of the skin, causing the lamellar interface direction to orient itself parallel to the skin surface. This effect will be spread throughout the talc layer deposited by the wicking of skin oils though the talc deposit and by the van der Waals forces causing inter-particle attraction. The stacked or oriented configuration thus represent the least energetic state. Because the area of contact with an applied skin surface is increased and because the surface is so flat, there is a greater tendency for the particles to "stick" to a skin surface, thus giving a very substantial rise to an increased skin adhesiveness over conventional talcs. In contrast, talc particles with irregular shapes, low aspect ratios and non-lamellar interface orientation exhibit low light transmission and almost no sustainable adhesion when applied to the skin.

Since the talc in accordance with the present invention has a greater tendency to align itself in a stacked orientation, in which particles of the talc lay flat one upon another, parallel to the surface to which it is applied, and due to its more extensive flat surfaces discussed above, the particles "slide" over one another more readily than the particles of a conventional talc. Further, due to the self orienting nature of the talc particles of the present invention, they tend to "slip" with respect to one another in a direction substantially parallel to an applied surface, such as a skin surface, when subjected to a force having a shearing component acting parallel to the skin surface. As a result, talc in accordance with the present invention exhibits better spreadability and significantly increased lubricity over conventional talcs.

It should be noted herein that due to its extreme softness, under conventional manufacturing processes, the fragile lamina structure of talc is invariably disrupted. Accordingly, talc particles in accordance with the present invention would have some staircase effects around the peripheral edges thereof. However, the peripheral surface is more curved, or rounded and less squared off than conventional talc. Such limited staircase effects are distinct from the stair case effects retained in conventional talcs discussed hereinabove in connection with FIGS. 9 and 10.

It should be noted that neither particle size nor bulk density are critical to the present invention. Rather, it is the shape of the talc particle relative to the lamellar interface direction which is critical. It should also be noted that any particular sample of talc in accordance with the present invention will have a distribution of particle sizes and shapes including those which would be encountered in conventional talcs. Accordingly, a talc sample in conformance with the present invention will have an appreciable percentage of particles, e.g., at least 10% having a smooth particle shape as defined above, such definition incorporating directionality relative to the lamellar interface and uniformity at its flat upper and lower surfaces.

Talc in accordance with the present invention can be used in any applications wherein conventional talcs have been used. For instance, it can be incorporated into various make up cosmetics such as foundations, face powders, face powder cakes, lipsticks, eye shadows, eye liners, and the like, and basic cosmetics such as creams, lotions and the like. Such cosmetics may be in the form of a powder, cake, emulsion, oil, gel or the like. Further, the talc of the present invention can be used in connection with pharmaceutical, medical devices and products, plastic modifiers, household products (e.g., soap, detergents, etc.), hair products, OTC products, antiperspirants, suntan lotions, acne remedies and antimicrobials. In utilizing the talc of the present invention in such applications, conventional talc can be completely or partially replaced by the talc of the present invention.

Cosmetics in accordance with the present invention and incorporating the talc of the present invention as a component, can be made by utilizing conventional methods for making cosmetics employing conventional talcs. For instance, the amount of the talc to be incorporated into a particular cosmetic can be determined by conventional methods for making such a cosmetic. However, the beneficial attributes of the present invention do permit cosmetic formulations to be varied to their betterment, as shall be described below (For example, the increased transparency of the talc permits a large reduction in pigment levels for pigmented products such as powder foundations, rouge or eyeshadow. This results in an overall increase in transparency of the powder foundations, rendering it particularly suitable for persons with dark complexions whose coloring is incompatible with opaque or high whiteness cosmetic products). Generally, cosmetic compositions in accordance with the present invention includes the talc of the present invention in the range of from 1.0% to 99.5% by weight and preferably in the range of from 5.0% to 70.0% by weight.

Products incorporating the talc of the present invention also exhibit the beneficial characteristics associated therewith. For instance, due to the increased skin adhesiveness, cosmetics incorporating the talc of the present invention exhibit increased skin adhesiveness. This eliminates the need for additional adhesive ingredients. In addition, due to the improved transparency of the talc of the present invention, cosmetics incorporating it contain 30 to 50% less coloring pigments to effectuate the level of coloring exhibited by conventional cosmetics, and as a result, exhibit greater transparency than conventional cosmetics. In addition, because of the talc's transparency, thinness, smoothness and lubricity, emollients added to enhance lubricity can be reduced depending upon formula.

Slip and lubricity are realized when applying a cosmetic product either via finger or sponge to the skin. Roughness is easily perceived by the consumer as drag, coarseness and scratchiness, especially when applying the product to the delicate eyelid as, for example, an eyeshadow. The slip of talc in accordance with the present invention exceeds that of conventionally produced talc and also that of sericite and mica, which are also utilized in this application.

Skin adhesion manifests itself in increased product-wear (i.e., an eyeshadow with talc in accordance with the present invention maintains a more uniform color and appearance for a longer period of time than a formulation made with conventional talc. Both properties of slip and adhesion are critical in designing decorative cosmetics and are critically important performance parameters when formulating a cosmetic product. These positive attributes are understood and valued by individuals trained in the art of cosmetology.

The improved slip and adhesion of the present invention in other than decorative cosmetics such as moisturizers, acne products, anti-perspirants, skin protectants, sun protective products are of similar importance and value to the consumer. Products containing the talc have improved product laydown and prolonged "active" adhesion which is supported by the extraordinary adhesion matrix of the present invention. Examples of an antiperspirant, acne and sunscreen product demonstrate the actual use of the present invention in these product categories.

Transparency of talc and cosmetic products is measured via coverage or whitening effect of the product on skin. High transparency is in most cases, beneficial, especially on tanned and dark skin tones in that the usual ashy appearance associated with conventional cosmetic products is avoided. Measurements of opacity can be done indirectly measuring for example brightness values of talc with a given quantity of black iron oxide in the talc and comparing the values to each other and to the brightness standard of MgO as a control. This method is state of the art. Another means of comparison-measurement could be done spectrophotometrically utilizing the same black oxide or another colorant measuring depth of shade. The present invention shows a significantly lower brightness value or a deeper shade respectively with the same quantity of color when comparing the values to samples produced with conventional talc. This indicates the talc to be more transparent than conventionally produced talcs.

Talc in accordance with the present invention may be used for topical human or veterinary applications, such as dry lubricants and adsorbents in external analgesic, antipruritic, skin protectant applications and as a carrier and fixative for active ingredients such as antimicrobials, insecticides, insect repellents, etc. Talc in accordance with the present invention, due to its slip and platelet shape is especially effective in modifying plastic films, bottles, etc. to modify their physical attributes. Wear tests of eyeshadow formulations containing the present invention have shown improved adhesion and overall uniformity when compared to formulations containing conventional talcs.

Other features of the present invention will become apparent in the course of the following descriptions of the exemplary embodiments which are given for illustration of the invention and are not intended to be limiting thereto. In the following examples, "DL talc" shall mean delaminated talc in accordance with the present invention.

THE TALC IN ACCORDANCE WITH THE PRESENT INVENTION

EXAMPLE 1

Delaminated talc in accordance with the present invention of a 100–200 mesh size and having a bulk density of 0.65 g/cc and a particle size in the range of 75 μm–150 μm (hereinafter referred to as "1M"). exhibits an extreme transparency which demonstrates itself as being much less opaque on either Caucasian, black or yellow skin than any other conventional talc.

When incorporated into a pressed powder foundation composition, the powder exhibited increased skin adhesiveness, better spreadability, increased lubricity, and greater transparency than foundations into which conventional talc is incorporated.

EXAMPLE 2

Delaminate talc of the present invention was processed into a long-wearing foundation having a 100–200 mesh size and a bulk density of 0.70 g/cc and a particle size in the range of 75 μm–150 μm (hereinafter referred to as "1R"). The DL talc exhibited extreme smoothness, slip and skin adhesion.

When incorporated into a pressed powder foundation composition, the powder exhibited increased skin adhesiveness, better spreadability, increased lubricity, and greater transparency than foundations into which conventional talc is incorporated and required 30–40% reduced pigment concentration to achieve equivalent depth of shade. This transparency is highly critical in pressed powder formulations and especially is pressed powder formulations for the black and hispanic population.

EXAMPLE 3

Delaminated talc in accordance with the present invention having a 200–325 mesh size and having a bulk density of 0.46 g/cc and a particle size in the range of 45 μm–75 μm (hereafter referred to as "2M") is extremely uniform and slippery when applied to skin.

When incorporated into a pressed powder foundation composition, the powder exhibited increased skin adhesiveness, better spreadability, increased lubricity, and greater transparency than foundations into which conventional talc is incorporated.

EXAMPLE 4

Talc particles in accordance with the present invention having a thickness of 10 μm, a 200–325 mesh sieve size, bulk density of 0.33 g/cc and a particle size in the range of 45 μm–75 μm (hereinafter referred to as "2R") are shown in FIG. 2. In examining the talc particle under a light microscope, a light coating of gold was evaporated at a high shadowing angle onto the talc particles. The angle was chosen such that the shadow area (indicated in FIG. 2 as bright areas around portions of the talc particles) has a length equal to ten times the thickness of the talc particle.

When incorporated into a pressed powder foundation composition, the powder exhibited a better feeling and, more particularly, increased skin adhesiveness, better spreadability, increased lubricity, and greater transparency than foundations into which conventional talc is incorporated.

COMPARATIVE EXAMPLE 4A

FIG. 3 shows particles of a conventional talc. In examining the talc particle under a light microscope, a light coating of gold was evaporated at a high shadowing angle onto the talc particles. The angle was chosen such that the shadow area (indicated in FIG. 3 as bright areas around portions of the talc particles) has a length equal to ten times the thickness of the talc particle.

The talc particles of Example 4 have substantially smooth and flat surfaces (see FIG. 2) compared to the talc particles of Comparative Example 4A which have rough edges (see FIG. 3). As a result, the talc particles of Example 4 appear to be more clear and therefore more transparent than the talc particles in Comparative Example 4A.

COMPARATIVE EXAMPLE 4B

FIG. 4 shows particles of another conventional talc. In examining the talc particle under a light microscope, a light coating of gold was evaporated at a high shadowing angle onto the talc particles. The angle was chosen such that the shadow area (indicated in FIG. 4 as bright areas around portions of the talc particles) has a length equal to ten times the thickness of the talc particle.

The talc particles of Example 4 have extremely smooth and flat surfaces (see FIG. 2) compared to the talc particles of Comparative Example 4B which have extremely rough edges indicated by saw-teeth-like shadow outer edges (see FIG. 4). As a result, the talc particles of Example 4 appear to be much clearer and therefore more transparent than the talc particles in Comparative Example 4B.

EXAMPLE 5

Delaminated talc in accordance with the present invention has a 200–325 mesh size, bulk density of 0.20 g/cc and a particle size in the range of 45 μm–75 μm (hereinafter "3R").

When incorporated into a pressed powder foundation composition, the powder exhibited increased skin adhesiveness, better spreadability, increased lubricity, and greater transparency than foundations into which conventional talc is incorporated.

EXAMPLE 6

Delaminated talc in accordance with the present invention has a 325–400 mesh size, having bulk density of 0.35 g/cc and a particle size in the range of 38 μm–45 μm (hereinafter referred to as "4M").

When incorporated into a pressed powder foundation composition, the powder exhibited increased skin adhesiveness, better spreadability, increased lubricity, and greater transparency than foundations into which conventional talc is incorporated.

EXAMPLE 7

Delaminated talc in accordance with the present invention has a 325 to 400 mesh size, bulk density of 0.18 g/cc and a particle size in the range of 38 μm–45 μm (hereinafter "4R").

When incorporated into a pressed powder foundation composition, the powder exhibited increased skin adhesiveness, better spreadability, increased lubricity, and greater transparency than foundations into which conventional talc is incorporated.

EXAMPLE 8

Delaminated talc in accordance with the present invention having bulk density of 0.19 g/cc, a sieve size less than 400 mesh and a particle size less than 38 μm (hereinafter referred to as "5M") when incorporated into a pressed powder foundation composition, produced a powder exhibiting increased skin adhesiveness, better spreadability, increased lubricity, and greater transparency than foundations into which conventional talc is incorporated.

COSMETIC COMPOSITIONS IN ACCORDANCE WITH THE PRESENT INVENTION

The following are examples of products produced incorporating DL talc, by the procedure listed to produce the product with the resultant attributes described.

EXAMPLE 9

LONG WEARING PRESSED POWDER (for a person having pale skin)

COMPOSITION

| Components | Range % by weight | Preferred % by weight |
|---|---|---|
| (1) DL Talc, 2M (See Example 5 above) (Filler/Matrix) | 70.0–90.0 | 90.5 |
| (2) Iron Oxide (Colorants) | .1–10.0 | .5 |
| (3) Polyethylene, Micronized | 2.0–6.0 | 3.0 |
| (4) Octyl Palmitate | 2.0–8.0 | 6.0 |
| (Liquid Binder) | | |
| | Total | 100.0 |

PRODUCT ATTRIBUTES: Transparent Pressed Powder with high lubricity and good adhesion.
PROCEDURE: Extend iron oxides on equal quantity of talc via pulverization, blend into remaining portion of talc and spray in the oilphase. Use state of the art equipment such as Gemco. Compress into pan utilizing pressures between 200 psi and 2000 psi ram pressure depending upon pan size.

EXAMPLE 10A

LONG WEARING PRESSED POWDER (for a person having dark skin)

COMPOSITION

| Components | Range % by weight | Preferred % by weight |
|---|---|---|
| (1) DL Talc, 3R (Ex. 5) (Filler/Matrix) | 70.00–90.00 | 74.50 |
| (2) Iron Oxides (Colorants) | 0.10–10.00 | 15.00 |
| (3) Zinc Stearate (Solid Binder) | 2.00–6.00 | 3.50 |
| (4) Mineral Oil 70 cst. | 2.00–9.00 | 7.00 |
| (Liquid Binder) | | |
| | Total | 100.0 |

PRODUCT ATTRIBUTES: Transparent pressed powder for a person having dark skin. It exhibits high lubricity and a prolonged wearing characteristic.
PROCEDURE: Same as above.

EXAMPLE 10B

CONVENTIONAL PRESSED POWDER (for a person having dark skin)

COMPOSITION

| Components | Range % by weight | Preferred % by weight |
|---|---|---|
| (1) Italian Talc, Filler/Matrix | 70.00–90.00 | 67.00 |
| (2) Iron Oxides (Colorants) | 0.10–30.00 | 22.50 |
| (3) Zinc Stearate (Solid Binder) | 2.00–6.00 | 3.50 |
| (4) Mineral Oil 70 cst. | 2.00–9.00 | 7.00 |
| (Liquid Binder) | | |
| | Total | 100.0 |

PRODUCT ATTRIBUTES: A pressed powder for a person having dark skin. It exhibits higher degree of opacity and lower wear characteristics. In addition, an increase of 40% in colorants was necessary to achieve similar depth in shade.
PROCEDURE: Same as above.

EXAMPLE 11

PRESSED EYESHADOW POWDER, MATTE

COMPOSITION

| Components | Range % by weight | Preferred % by weight |
|---|---|---|
| (1) DL Talc, 4M (Ex. 6) (Filler/Matrix) | 60.00–90.00 | 64.70 |
| (2) Iron Oxides (Colorants) | 0.50–10.00 | 2.60 |
| (3) Ultramarine Blue (Colorants) | 0.00–25.00 | 20.00 |
| (4) Methyl Paraben (Preservative) | 0.10–.50 | .20 |
| (5) Zinc Stearate (Solid Binder) | 0.50–6.00 | 2.00 |
| (6) Octyl Palmitate (Liquid Binder) | 3.00–7.00 | 7.00 |
| (7) Squalane (Liquid Binder) | 1.00–5.00 | 3.50 |
| | Total | 100.0 |

PRODUCT ATTRIBUTES: Soft, smooth, lubricous eye shadow powder with good adhesion and wear.
PROCEDURE: Combine colors, preservatives and Zn stearate with equal portion of talc, pulverize and blend with remaining portion of talc. Spray oilphase while mixing into powder. Compress into suitable godets.

EXAMPLE 12

PRESSED EYESHODOW POWDER, FROST

COMPOSITION

| Components | Range % by weight | Preferred % by weight |
|---|---|---|
| (1) DL Talc, 1R (Ex. 2) (Filler/matrix) | 40.00–80.00 | 55.50 |
| (2) TIO2 and Mica (Pearl) | 10.00–40.00 | 25.00 |
| (3) Zinc Stearate (Solid Binder) | 2.00–4.00 | 3.00 |
| (4) Magnesium Stearate (Solid Binder) | 1.00–5.00 | 2.00 |
| (5) Methyl Paraben (Preservative) | 0.10–0.30 | — |
| (6) Ultramarine Blue (Colorants) | 1.00–5.00 | 5.00 |

COMPOSITION -continued

| Components | Range % by weight | Preferred % by weight |
|---|---|---|
| (7) Iron Oxides (Colorants) | 0.50–5.00 | .50 |
| (8) Dimethicone 350 cst. | 6.00–13.00 | 10.00 |
| (Liquid Binder) | | |
| Total | | 100.0 |

PROCEDURE: Combine colors, preservatives and stearates with equal amount of talc, pulverize through hammer-mill, blend with remaining talc and pearl, spray oilphase onto batch while blending powder. Compress into suitable pans.

EXAMPLE 13

LIQUID/CREAM MAKE-UP

COMPOSITION

| Components | Range % by weight | Preferred % by weight |
|---|---|---|
| (1) Deionized water (Vehicle) | QS | QS |
| (2) Hydroxethyl Cellulose (Gum) | .10–.40 | .20 |
| (3) Xanthan Gum (Gum) | .40–.40 | .20 |
| (4) Butylene Glycol (Humectant) | .00–8.00 | 5.00 |
| (5) Lecithin (Emulsifier) | .00–1.50 | 1.00 |
| (6) Polysorbate 20 (Emulsifier) | .00–1.50 | 1.00 |
| (7) Methyl Paraben (Preservatives) | .10–.30 | .20 |
| (8) Iron Oxides (Colorants) | .10–8.00 | 1.90 |
| (9) Titanium Dioxide (Colorants) | .00–13.00 | 7.00 |
| (10) DL Talc 5M (Ex. 8) (Filler/Matrix) | 1.00–15.00 | 8.00 |
| (11) Capric/Caprylic Triglyceride (Emollient) | 1.0–8.00 | 5.00 |
| (12) Isoporpyl Myristate (Emollient) | 1.00–8.00 | 5.00 |
| (13) Squalane (Emollient) | .00–5.00 | 2.00 |
| (14) Stearic Acid (Emulsifier) | .50–3.00 | 2.00 |
| (15) SE Glycerol Mono Stearate (Emulsifier) | 1.00–4.00 | 2.00 |
| (16) Cetyl Alcohol (Emulsifier) | .20–1.00 | .50 |
| (17) Fragrance | .00–.20 | — |
| (18) Additional Preservatives | .00–.50 | .20 |
| Total | | 100.0 |

PRODUCT ATTRIBUTES: Liquid make-up with excellent slip, DL talc helps wear and non-tacky feel of product.

PROCEDURE: Charge deionized water into kettle, add ingredients to water sequentially while homogenizing water phase to completely disperse gums and pigments. The pigments should be pulverized prior to addition. Heat phase to 75 degrees C. Combine oil phase, heat to 70 degrees C., add to waterphase while homogenizing, when uniform cool to 35 degrees C., add fragrance and preservatives while sweepmixing. Drop batch at 28 degrees C. and fill into suitable containers.

EXAMPLE 14

LIPSTICK, MATTE

COMPOSITION

| Components | Range % by weight | Preferred % by weight |
|---|---|---|
| (1) Candelilla Wax (Wax) | 4.00–9.00 | 8.00 |
| (2) Ozokerite (Wax) | 1.00–4.00 | 2.00 |
| (3) Paraffin Wax (Wax) | 2.00–5.00 | 5.00 |
| (4) Isostearyl Isostearate (Emollient) | 2.00–10.00 | 10.00 |
| (5) Capric/Caprylic Triglyceride (Emollient) | 2.00–10.00 | 10.00 |
| (6) Castor Oil (Emollient) | QS | 52.60 |
| (7) Propyl Paraben (Preservatives) | .10 | .10 |
| (8) Tocopheryl Acetate (Antioxidant) | .10–1.00 | .10 |
| (9) Colorants | | |
| D&C Red #6 BA Lake | .00–4.00 | .40 |
| D&C Red #7 CA Lake | .00–4.00 | .30 |
| Red Oxide | .00–3.00 | 1.50 |
| (10) DL Talc 4M (Ex. 6) | 2.00–10.00 | 10.00 |
| (Filler/Matrix) | | |
| Total | | 100.0 |

PROCEDURE: Combine all ingredients and melt to 75 degrees C., colorants should be ground in castor oil prior to addition, blend with a lightning type propeller mixer until melt is uniform. Pour into lipstick molds, allow to cool, assemble into lipstick-case, flame to high surface gloss and close.

EXAMPLE 15

EYESHADOW STICK

COMPOSITION

| Components | Range % by weight | Preferred % by weight |
|---|---|---|
| (1) Ozokerite (Wax) | .50–6.00 | 2.00 |
| (2) Cetyl Alcohol (Wax) | 1.00–4.00 | 2.00 |
| (3) C 28 Alcohol (Wax) | 1.00–6.00 | 5.00 |
| (4) Cyclomethicone D 5 (Emollient) | QS | QS |
| (5) Methyl Paraben (Preservatives) | .20 | .20 |
| (6) Pigments/Colorants | 1.00–20.00 | 15.00 |
| (7) Octyl dodecanol (Emollient) | 5.00–20.00 | 10.00 |
| (8) DL Talc 3R (Ex. 5) | 5.00–25.00 | 15.00 |
| (Filler/Matrix) | | |
| Total | | 100.0 |

PRODUCT ATTRIBUTES: Long wearing eye shadow stick. DL Talc facilitates even product laydown and coloration and prolonged wear.

PROCEDURE: Combine ingredients, melt to 85 degrees C., pigments need grinding to be fully deglomerated. When uniform pour into molds and assemble into sealed container.

EXAMPLE 16

LONG WEARING LIPSTICK

COMPOSITION

| Components | Range % by weight | Preferred % by weight |
|---|---|---|
| (1) Synthetic Wax | 3.00–8.00 | 3.00 |
| (2) Ozokerite (Wax) | 4.00–10.00 | 5.00 |
| (3) Cetyl Esters (Wax) | 2.00–5.00 | 3.00 |
| (4) Trilaurin (Wax) | 2.00–5.00 | 4.00 |
| (5) Octyl Dodecanol (Emollient) | 2.00–20.00 | 5.00 |
| (6) ISO Dodecane (Emollient) | 4.00–12.00 | 10.00 |
| (7) Cyclomethicone D5 (Emollient) | 10.00–60.00 | 53.95 |
| (8) Colorants | | |
| D&C Red 7 CA-Lake | .00–5.00 | .40 |
| Red 6 BA-Lake | .00–5.00 | .30 |
| Red Iron Oxide | .00–10.00 | 2.00 |
| Black Iron Oxide | .00–3.00 | .05 |
| (9) DL Talc 4M - (Ex. 6) (Filler/Matrix) | 5.00–20.00 | 12.00 |
| Total | | 100.0 |

ATTRIBUTES: "DL Talc" acts as a fixative for product resulting in long wear.

PROCEDURE: Combine waxes and melt in a suitable vessel. Grind colorants on suitable mill such as rollermill to particle size of less than 1 mil. (Hegman Gauge) and add to batch. Maintain temperature at 80 degrees C., use lightnin mixing, avoid solvent loss. When uniform pour into molds, allow to cool and assemble into cosmetic cases that are hermetically sealed to prevent volatile solvent loss.

EXAMPLE 17

ANTIPERSPIRANT STICK

COMPOSITION

| Components | Range % by weight | Preferred % by weight |
|---|---|---|
| (1) Cyclomethicone D4 (Emollient) | 40.00–60.00 | 52.00 |
| (2) Isopropyl Myristate (Emollient) | 2.00–10.00 | 3.00 |
| (3) Stearyl Alcohol (Wax) | 15.00–20.00 | 18.00 |
| (4) PEG-8 Distearate (Emollient) | 1.00–5.00 | 2.00 |
| (5) Aluminum Chloro Hydrate, Impalpable ("Active" Antiperspirant Agent) | 10.00–22.00 | 20.00 |
| (6) DL Talc 5M - (Ex. 8) (Filler/Matrix) | 2.00–8.00 | 5.00 |
| Total | | 100.0 |

ATTRIBUTES: "DL TALC" is the fixative for the active.
PROCEDURE: Intensely blend the aluminum chlor hydrate in cyclomethicone to a uniform paste utilizing a Cowles dissolver. In a suitable kettle melt waxes and stearyl alcohol, add grind while mixing until uniform, maintain temperature at 65 degrees C. to 70 degrees C., pour into suitable antiperspirant cases and cool to RT.

EXAMPLE 18A

CREAM EYESHADOW COMPARISON WITH CONVENTIONAL TALC FORMULATION

COMPOSITION

| Components | Range % by weight | Preferred % by weight |
|---|---|---|
| (1) DL Talcs (Filler/Matrix) | 50.00–85.00 | 79.90 |
| (2) Magnesium Stearate (Solid Binder) | 0.50–5.00 | 2.00 |
| (3) Polyethylene, Micronized (Solid Binder) | 0.50–5.00 | 2.00 |
| (4) Black Iron Oxide (Colorants) | 0.00–20.00 | 8.00 |
| (5) Brown Iron Oxide (Colorants) | 0.00–8.00 | 4.00 |
| (6) Yellow Iron Oxide (Colorants) | 0.00–20.00 | 0.90 |
| (7) Methyl Paraben (Preservatives) | 0.00–0.30 | 0.20 |
| (8) Octyl Palmitate (Liquid Binder) | 1.00–5.00 | 3.00 |
| Total | | 100.0 |

EXAMPLE 18B

CREAM EYESHADOW COMPARISON WITH CONVENTIONAL TALC FORMULATION

COMPOSITION

| Components | Range % by weight | Preferred % by weight |
|---|---|---|
| (1) DL Talcs (Filler/Matrix) | 50.00–85.00 | 85.06 |
| (2) Magnesium Stearate (Solid Binder) | 0.50–5.00 | 2.00 |
| (3) Polyethylene, Micronized (Solid Binder) | 0.50–5.00 | 2.00 |
| (4) Black Iron Oxide (Colorants) | 0.00–20.00 | 4.80 |
| (5) Brown Iron Oxide (Colorants) | 0.00–8.00 | 2.40 |
| (6) Yellow Iron Oxide (Colorants) | 0.00–20.00 | 0.54 |
| (7) Methyl Paraben (Preservatives) | 0.00–0.30 | 0.20 |
| (8) Octyl Palmitate (Liquid Binder) | 1.00–5.00 | 3.00 |
| Total | | 100.0 |

COMPOSITION

| Components | % by weight |
|---|---|
| COMPARISON EXAMPLE 18C: CREAM EYESHADOW CONVENTIONAL TALC | |
| (1) Italian Talc | 79.90 |
| (2) Magnesium Stearate | 2.00 |
| (3) Polyethylene, Micronized | 2.00 |
| (4) Black Iron Oxide | 8.00 |
| (5) Brown Iron Oxide | 4.00 |
| (6) Yellow Iron Oxide | 0.90 |
| (7) Methyl Palmitate | 0.20 |
| (8) Octyl Palmitate | 3.00 |
| Total | 100.0 |

-continued

COMPARISON EXAMPLE 18D: CREAM EYESHADOW CONVENTIONAL TALC

| Components | |
|---|---|
| (1) Montana Talc | 79.90 |
| (2) Magnesium Stearate | 2.00 |
| (3) Polyethylene, Micronized | 2.00 |
| (4) Black Iron Oxide | 8.00 |
| (5) Brown Iron Oxide | 4.00 |
| (6) Yellow Iron Oxide | 0.90 |
| (7) Methyl Palmitate | 0.20 |
| (8) Octyl Palmitate | 3.00 |
| Total | 100.0 |

ATTRIBUTES: "DL TALC" improves adhesion and wear when comparing formulations in wear tests. Also the DL TALC formulations are deeper in shade indicating them to be of lower opacity than conventional talcs. The cream eyeshadow of Example 18B is especially suitable for a person having dark skin complexion PROCEDURE: Intensely blend and pulverize iron oxides, methyl paraben, Mg Stearate and PE with equal amount of talc. Blend with remaining portion of talc and sray in the octyl palmitate. Assure lumpfree dispersion. Press into suitable godets at pressures ranging from 200 psi to 800 psi.

EXAMPLE 19

CREAM BLUSH

COMPOSITION

| Components | Range % by weight | Preferred % by weight |
|---|---|---|
| (1) DL Talc 5M - (Ex. 8) (Filler/matrix) | 20.00–60.00 | QS |
| (2) DL Talc 3M - (Ex. 3) (Filler/matrix) | 5.00–20.00 | 15.00 |
| (3) Polyethylene, Micronized (Solid Binder) | .50–5.00 | 3.00 |
| (4) Zinc Stearate (Solid Binder) | .50–5.00 | 2.00 |
| (5) Titanium Dioxide (Colorants) | .00–10.00 | .40 |
| (6) Yellow Iron Oxide (Colorants) | .00–10.00 | .18 |
| (7) Red Iron Oxide (Colorants) | .00–10.00 | .08 |
| (8) Black Iron Oxide (Colorants) | .00–1.00 | .006 |
| (9) D&C Red #7, CA Lake (Colorants) | .00–4.00 | — |
| (10) Nylon 12 (Dry Binder) | .00–20.00 | 18.00 |
| (11) Octyl Dodecyl Steroyl Stearate (Liquid Binder) | .00–4.00 | — |
| (12) Propylene Glycol Dicaprylate/Dicaprate (Liquid Binder) | .00–4.00 | — |
| (13) Dimethicone 10 cst. (Liquid Binder) | 5.00–20.00 | 14.00 |
| (14) Phenoxyethanol (Preservatives) | .00–1.00 | .50 |
| (15) Dimethicone 350 cst. (Liquid Binder) | .00–15.00 | 1.50 |
| Total | | 100.0 |

PROCEDURE: Combine colorants, PE, Zn Stearate with equal amount of DL TALC 5M, pulverize and blend into remaining portion or talcs and nylon. Spray combined oils into blend and mix until uniform. Conventional powder equipment such as Patterson Kelly, Gemco or other can be used. Compress into suitable pans at pressures of 1000 to 2000 psi Ram Pressures.

EXAMPLE 20

DUSTING POWDER

COMPOSITION

| Components | Range % by weight | Preferred % by weight |
|---|---|---|
| (1) DL Talc 5M (Ex. 8) (Filler/Matrix) | 85.0–98.0 | 95.0 |
| (2) Magnesium Carbonate | 2.0–15.0 | 3.0 |
| (3) Fragrance | .2–5.0 | 3.0 |
| Total | | 100.0 |

ATTRIBUTES: Talc is carrier for fragrance.
PROCEDURE: Combine fragrance with Mg CO3, sieve into talc while tumble blending in ribbon blender or equivalent equipment.

EXAMPLE 21

SUNSCREEN LOTION

COMPOSITION

| Components | Range % by weight | Preferred % by weight |
|---|---|---|
| (1) Deionized Water | QS | QS |
| (2) Hydroxy Ethyl Cellulose (Gum) | .10–1.00 | .20 |
| (3) Xanthan Gum (Gum) | .10–1.00 | .20 |
| (4) Glycerine | .10–5.00 | 4.00 |
| (5) PEG-20 Methyl Glucose Sesquistearate (Emulsifier) | .10–2.00 | .50 |
| (6) Methyl Paraben (Preservatives) | .05–.50 | .20 |
| (7) Triethanolamine, 99% (Er as soap) | .10–1.00 | .50 |
| (8) Isopropyl Palmitate (Emollient) | 2.00–7.00 | 4.00 |
| (9) Capric/Caprylic Triglyceride (Emollient) | 2.00–10.00 | 3.00 |
| (10) Octyl Salicylate (Sunscreen) | .00–5.00 | 5.00 |
| (11) Octyl Methoxy Cinnamate (Sunscreen) | 3.00–7.50 | 6.00 |
| (12) Benzophenone - 3 (Sunscreen) | 1.00–5.00 | 2.00 |
| (13) SE Glycerol Mono Stearate (Emulsifier) | 1.00–5.00 | 4.00 |
| (14) Cetyl Alcohol (Emulsifier) | .10–1.50 | .50 |
| (15) Dimethicone 350 cst. (Emollient) | .50–2.00 | 1.00 |
| (16) Stearic Acid (Emulsifier) | .10–3.00 | 1.00 |
| (17) Tocopheryl Acetate (Antioxidant) | .05–1.00 | .10 |
| (18) DL Talc 2M - (Ex. 3) (Filler/Matrix) | 2.00–10.00 | 8.00 |
| (19) Deionized Water (Vehicle) | 2.00–10.00 | 8.00 |
| (20) Preservative | .00–2.00 | .20 |
| (21) Fragrance | .00–1.00 | — |
| Total | | 100.0 |

ATTRIBUTES: Soft liquid/cream with sunscreen. DL Talc acts as fixative for SPF ingredients.

PROCEDURE: Charge water into suitable kettle, add sequentially ingredients of water phase with moderate agitation. Heat phase to 75 degrees C. Combine oil phase ingredients and heat to 70 degrees C. while stirring until homogeneous. Add oil phase to water phase while homogenizing. Allow to cool while mixing, add predispersed DL Talc and water to combined batch at 40 degrees C., add preservatives and fragrance, cool further to 28 degrees C. and fill into suitable containers.

EXAMPLE 22

ANTI ACNE LOTION

COMPOSITION

| Components | Range % by weight | Preferred % by weight |
|---|---|---|
| (1) Deionized Water (Vehicle) | QS | QS |
| (2) CMC, Carboxy Methyl Cellulose (Gum) | .05–1.00 | .20 |
| (3) Sclerotium Gum (Gum) | .10–1.00 | .50 |
| (4) Butylene Glycol (Humectant) | 1.00–8.00 | 5.00 |
| (5) Polysorbate 20 (Emulsifier) | .10–2.00 | .80 |
| (6) Sodium Hydroxide (Alkali to neutralize Acid) | .01–1.00 | .20 |
| (7) Methyl Paraben (Preservatives) | .10–.50 | .20 |
| (8) Se Glycerol Mono Stearate (Emulsifier) | 1.00–5.00 | 4.00 |
| (9) Propylene Glycol Dicaprylate/Dicaprate (Emollient) | 2.00–10.00 | 8.00 |
| (10) Salicylic Acid (Active Keratolytic Agent) | .50–2.00 | 2.00 |
| (11) Propyl Paraben (Preservative) | .05–.20 | .10 |
| (12) Cetyl Alcohol (Emulsifier) | .20–2.00 | 1.00 |
| (13) DL Talc 5M (Ex. 8) (Filler/Matrix) | 2.00–10.00 | 6.00 |
| (14) Polysorbate 20 (Emulsifier) | .05–.50 | .20 |
| (15) Isopropanol (Vehicle) | 2.00–10.00 | 6.00 |
| Total | | 100.0 |

ATTRIBUTES: Soft lotion having Keratolytic action helping to fight symptoms of acne.
PROCEDURE: Charge water into suitable kettle, add ingredients of water phase and blend until homogeneous. Heat to 75 degrees C. Combine ingredients of oil phase, heat to 70 degrees C. and add to water phase while homogenizing. Blend until emulsion is formed and homogeneous, cool to 40 degrees C., add predispersed DL Talc in isopropanol, cool further to 28 degrees C. Fill into suitable containers.

It will be understood that the embodiments described herein are merely exemplary and that a person skilled in the art may make many variations and modifications without departing from the spirit and scope of the invention. All such variations and modifications are intended to be included within the scope of the invention as defined in the appended claims.

We claim:

1. A delaminated talc, comprising talc particles at least 10% of which have an aspect ratio of 5 or greater, the aspect ratio of each of said particles determined by dividing said particle's extent along an upper surface thereof by said particle's thickness, said upper surface being substantially parallel to a lamellar interface direction and said thickness being measured perpendicularly to said lamellar interface direction, said at least 10% of said talc particles having substantially parallel, smooth top and bottom surfaces with comparably sized respective surface areas and an outer peripheral surface defining a profile of said particles which can be approximated by a set of connected curves having a radii of curvature greater than $0.125 \, D_S$.

2. The talc of claim 1, wherein said outer peripheral surface is substantially smooth and perpendicular to said interface direction, said smoothness being perceptible when measured at the magnitude of dimensionality of said upper surface extent.

3. The talc of claim 1, wherein said particles have a substantially smooth bottom surface substantially parallel to said top surface and having an extent approximating the extent of said top surface.

4. The talc of claim 2, wherein the profile formed by said outer peripheral surface is substantially devoid of acute angularity and sharp edges when measured at the magnitude of dimensionality of said upper surface extent.

5. The talc of claim 1, wherein said at least 10% of said talc particles have the general shape characteristics depicted in FIGS. 2, 5 and 6.

6. The talc of claim 1, wherein said talc displays transparency, skin adhesiveness, lubricity and spreadability when applied as a film to human skin.

7. The talc of claim 1, wherein at least 50% of said talc particles fall within the size range of 75 μm to 150 μm.

8. The talc of claim 1, wherein at least 50% of said talc particles fall within the size range of 45 μm to 75 μm.

9. The talc of claim 1, wherein at least 50% of said talc particles fall within the size range of 38 μm to 45 μm.

10. The talc of claim 1, wherein said talc is substantially transparent when applied as a film to human skin.

* * * * *